United States Patent
Paufique

(10) Patent No.: US 11,382,858 B2
(45) Date of Patent: Jul. 12, 2022

(54) **ACTIVE INGREDIENT OBTAINED FROM *NYMPHAEA ALBA* FLOWERS**

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 0 days.

(21) Appl. No.: 16/912,958

(22) Filed: Jun. 26, 2020

(65) Prior Publication Data

US 2020/0405622 A1     Dec. 31, 2020

(30) Foreign Application Priority Data

Jun. 28, 2019    (FR) ...................................... 1907118

(51) Int. Cl.
*A61K 36/00* (2006.01)
*A61K 8/9789* (2017.01)
*A61Q 19/00* (2006.01)

(52) U.S. Cl.
CPC ............ *A61K 8/9789* (2017.08); *A61Q 19/00* (2013.01)

(58) Field of Classification Search
CPC ........ A61Q 19/02; A61Q 19/08; A61Q 19/00; A61K 8/60
See application file for complete search history.

(56) References Cited

U.S. PATENT DOCUMENTS

| | | |
|---|---|---|
| 2002/0004080 A1 | 1/2002 | Paufique |
| 2008/0287552 A1 | 11/2008 | Paufique |
| 2016/0074455 A1 | 3/2016 | Paufique |

FOREIGN PATENT DOCUMENTS

| | | |
|---|---|---|
| CN | 104365921 A * | 2/2015 |
| CN | 106562910 A | 4/2017 |
| FR | 2808442 A1 | 11/2001 |
| FR | 2893504 A1 | 5/2007 |
| FR | 2989276 A1 | 10/2013 |
| FR | 3025424 A1 | 11/2016 |
| FR | 3058057 A1 | 4/2018 |

OTHER PUBLICATIONS

Abarike et al., "Exploring the Nutrient Potential of *Nymphaea alba* (Water Lilly), for use as Liverstock Feed", UDS International Journal of Development (UDSIJD), Aug. 2015, pp. 1-11, vol. 2, No. 1.
CV Skinlabs, "How White Water Lily Benefits the Skin", Sep. 17, 2018, pp. 1-6, http://cvskinlabs.com/how-white-water-lily-benefits-the-skin/.
Jambor et al., "Flavonois From the Flowers of *Nymphaea alba* L.", ACTA Societatis Botanicorum Poloniae, (1991), pp. 119-125, vol. 60, No. 1-2.
"Active Ingredients—Nympheline", Aug. 27, 2010, pp. 8-17, XP055038817.
Puri M. et al., "Enzyme-assisted extraction of bioactives from plants", Trends in Biotechnology, Jan. 2012, pp. 37-44, vol. 30, No. 1.

* cited by examiner

*Primary Examiner* — Qiuwen Mi

(74) *Attorney, Agent, or Firm* — Greer, Burns & Crain, Ltd.

(57) ABSTRACT

The subject matter of the invention is a cosmetic active ingredient comprising at least one hydrolysate of *Nymphaea alba* flowers, as well as cosmetic compositions including said active ingredient and its use in cosmetics. In particular, the invention relates to the use of an extract of *Nymphaea alba* flowers for improving skin complexion.

15 Claims, No Drawings

ACTIVE INGREDIENT OBTAINED FROM *NYMPHAEA ALBA* FLOWERS

CROSS-REFERENCE TO RELATED APPLICATIONS

This application claims the benefit of priority to French Patent Application FR 1907118 filed Jun. 28, 2019, the entire disclosure of which is incorporated herein by reference.

TECHNICAL FIELD

The invention relates to a specific cosmetic active ingredient obtained from *Nymphaea alba* flowers, as well as to the use of *Nymphaea alba* flower extracts in cosmetics, particularly for obtaining an even and bright complexion radiance.

BACKGROUND

Complexion radiance is an indicator of good health and of a healthy lifestyle, and the appearance of the skin, which is considered to be an essential component of beauty, is a widespread concern, particularly among women.

However, the skin faces daily challenges: tobacco, pollution, alcohol abuse, sedentary lifestyle, fatigue or even stress are all factors that influence its quality and radiance.

Several products exist that are intended to act on complexion radiance, but many are non-natural products and/or have limited effectiveness.

The object of the invention is to provide a solution originating from a natural raw material capable of effectively improving complexion radiance.

To this end, the invention proposes the use of a cosmetic active ingredient comprising at least one extract obtained from *Nymphaea alba* flowers.

The water lily is an aquatic plant, found in ponds, pools, rivers, in the wild or as an introduced species. Referred to as "nymphea", which means water god, by popular tradition, the water lily is revered not only for the delicacy and purity of its beautiful white flowers, but also for its many medicinal powers. The plant has a special anatomical feature since it has "floats" in its peduncles and in its petioles. Reference is made to air gaps because its tissues are able to store gases and thus allow the flower to float on the surface.

Water lily flowers are known for their sedative, soothing and anaphrodisiac properties. They are recommended particularly in cases of insomnia, anxiety and stress. These properties are mainly due to the sesquiterpene alkaloids richness of these plants.

SUMMARY

Several extracts that are obtained from these flowers have already been described for their use in cosmetics with anti-oxidant, anti-inflammatory or even soothing activities.

However, surprisingly, *Nymphaea alba* flower extracts, when they are applied to the skin of healthy individuals, can effectively improve complexion radiance.

Therefore, the subject matter of the invention is the cosmetic use, topically applied to the skin of a healthy individual, for improving complexion radiance, of a cosmetic active ingredient comprising at least one extract of *Nymphaea alba* flowers or of a composition comprising such an active ingredient.

The invention also relates to a particular cosmetic active ingredient, namely a cosmetic active ingredient comprising at least one hydrolysate of *Nymphaea alba* flowers, as well as its cosmetic use in topical application to the skin of a healthy individual, for improving the condition of the skin and particularly for improving complexion radiance.

The subject matter of the invention is also a method for obtaining such an active ingredient.

The invention also relates to compositions including such an ingredient and to a cosmetic method for improving complexion radiance that involves applying such compositions to the skin.

DETAILED DESCRIPTION

The invention will now be described in detail.

Definitions

The term "cosmetic active agent" or "cosmetic active ingredient", within the meaning of the invention, relates to at least one compound preferably a set of compounds, having a cosmetic effect on the skin.

The term "*Nymphaea alba*", within the meaning of the present invention, is understood to mean a water lily or its substitutes: *Castalia alba* (L) Greene, *Castalia minoriflora* Simonk, *Castalia speciosa* Salisb, *Nymphaea occidentalis* Mos or *Nymphaea minoriflora* (Simonk.) Wissjul. The term "*Nymphaea alba*", within the meaning of the invention, is not understood to mean the lotus or *Nelumbo nucifera*.

The term "hydrolysate" of *Nymphaea alba*, within the meaning of the invention, is understood to mean any extract, including an aqueous extract, obtained from *Nymphaea alba* using a method comprising at least one enzymatic or chemical hydrolysis step.

The term "enzymatic hydrolysate" of *Nymphaea alba*, within the meaning of the invention, is understood to mean any extract obtained from *Nymphaea alba* using a method comprising at least one enzymatic hydrolysis step.

According to a first aspect, the invention thus relates to the use of cosmetic active ingredients comprising at least one hydrolysate obtained from *Nymphaea alba* flowers for improving complexion radiance.

A radiant complexion results from a bright effect and a slightly pink colored effect, for Caucasian skin. Skin radiance is directly related to the phenomena of diffusion and reflection of light on the surface of the skin, with the color of the skin mainly originating from the light that it reflects.

According to the invention, the use, on the skin of a healthy individual by topical application, of an active ingredient comprising at least one hydrolysate obtained from *Nymphaea alba* flowers or of a composition containing said active ingredient, enables complexion radiance to be improved by acting on the skin grain, the transparency, the radiance and the light pink color of the skin. According to the invention, an active ingredient comprising at least one hydrolysate obtained from *Nymphaea alba* flowers is capable of acting on these parameters. Thus, preferably, an active ingredient comprising at least one hydrolysate obtained from *Nymphaea alba* flowers or from a composition containing said active ingredient is used for evening out the skin complexion and/or for making the skin complexion more transparent and/or for making the skin complexion brighter and/or for lightening the skin complexion and/or for refining the skin grain.

In addition, for optimal reflection and diffusion of light, the skin needs to be smooth, clean and homogeneous. The smoother the cutaneous microrelief, the more homogeneous the diffusion of light and the more radiant the complexion. According to the invention, an active ingredient comprising at least one extract, preferably an aqueous extract, obtained from *Nymphaea alba* flowers is capable of smoothing the cutaneous microrelief. Thus, preferably, an active ingredient comprising at least one extract obtained from *Nymphaea alba* flowers or from a composition containing said active ingredient is used for smoothing the cutaneous microrelief, in particular by reducing the roughness parameters of the skin.

In addition, the influence of environmental stresses such as UVs, can lead to carbonylation of proteins. This modification of the protein structure is irreversible and leads to a reduction in the light transmission of the *Stratum corneum*. The active ingredient according to the invention is capable of acting on the quality of the appearance of the skin, by limiting the formation of oxidized proteins. Thus, preferably, an active ingredient comprising at least one hydrolysate obtained from *Nymphaea alba* flowers or from a composition containing said active ingredient is used to also lessen any skin wrinkles and/or to soften the skin.

According to another aspect, the aim of the invention is a specific active ingredient, which is particularly useful for all the uses that are the subject matter of the invention described above.

Said active ingredient is a cosmetic active ingredient comprising at least one hydrolysate obtained from *Nymphaea alba* flowers. Preferably, it is an enzymatic hydrolysate, obtained from a method comprising at least one enzymatic hydrolysis, even more preferably from a method comprising at least two enzymatic hydrolyses, and particularly from a method comprising at least two enzymatic hydrolyses carried out with different types of enzymes.

Preferably, the active ingredient according to the invention comprises at least:
carbohydrates;
minerals;
proteins.

The content of carbohydrates in the active ingredient can be determined by the DUBOIS method (Dubois M et al., Analytical Chemistry, 28, 3, 350-356, 1956). It is expressed as a percentage of the dry matter content.

The protein fraction of the active ingredient according to the invention can be determined by the LOWRY method (Lowry et al., Protein measurement with the Folin reagent, J. Biol. Chem., 193, 265, 1951). It is expressed as a percentage of the dry matter content. In addition, FPLC type chromatography can allow the size of the peptide compounds that are present to be determined.

The content of crude ash (minerals) can be determined by weighing the residues resulting from the incineration of the samples of the active ingredient according to the invention at 550° C., in an electric muffle furnace. It is expressed as a percentage of dry matter content.

The content of polyphenolic compounds can be determined according to the following method. The polyphenolic compounds form, in the presence of potassium ferricyanide, colored compounds, detectable at 715 nm. The coloring intensity is proportional to the quantity of polyphenolic compounds. Readings are taken from a standard sample of gallic acid ranging between 40 and 120 mg/l. The results obtained for the samples allow a straight-line optical density to be traced as a function of the concentration and the polyphenols level of the samples is read directly on this straight line. The content of polyphenolic compounds of the hydrolysate according to the invention is preferably expressed as a percentage of gallic acid equivalent relative to the dry matter content of the hydrolysate according to the invention.

The active ingredient and the hydrolysate according to the invention can be in solid form or in liquid form.

When it is in liquid form, the active ingredient according to the invention is preferably exclusively formed by the hydrolysate obtained from water lily flowers.

The liquid hydrolysate is preferably in the form of a clear liquid, with a low odor and a yellow color. It can, however, be more colored and/or discolored using any method known to a person skilled in the art.

Preferably, the liquid hydrolysate according to the invention has a dry matter content of: 22 to 55 g/l, even more preferably 24 to 35 g/l.

When it is in solid form, particularly in powder form, the active ingredient according to the invention is formed by the hydrolysate as described above and by a carrier, such as maltodextrins, for example. In this case, preferably, the hydrolysate represents at least 10% by weight of the active ingredient and the carrier represents at most 90%.

According to a preferred embodiment, the active ingredient has at least one of the following features, or a combination of at least two of the following features, preferably at least all the following features:
the comprises at least 23% of carbohydrates by weight of dry matter of the hydrolysate;
the total sugar content in the liquid hydrolysate assayed by the Dubois method is 7 to 23 g/L, preferably 8 to 15 g/l, i.e. 23 to 62% by total weight of dry matter;
the hydrolysate comprises at least 30% of minerals (ash content) by weight of dry matter of the hydrolysate;
the hydrolysate comprises at least 8% of peptides by weight of dry matter of the hydrolysate;
the peptides present in the hydrolysate have molar masses of less than 2000 Da, by weight of dry matter of the hydrolysate;
the hydrolysate comprises at least 8% by weight of dry matter of the hydrolysate of peptides having molar masses of less than 2000 Da,
the hydrolysate comprises less than 0.2% of polyphenolic compounds by weight of dry matter of the hydrolysate.

According to a particularly suitable embodiment, the active ingredient according to the invention is obtained by implementing the following steps:
solubilization of *Nymphaea alba* flower powder in water;
at least one enzymatic hydrolysis, preferably at least two enzymatic hydrolyses, even more preferably at least two enzymatic hydrolyses carried out using at least two different types of enzymes;
separation of the soluble and insoluble phases;
enzymatic inactivation by heat treatment;
filtrations; and/or sterilizing filtration.

An additional step of drying the hydrolysate can be added so that it is in solid form, preferably in powder form. It can be a lyophilization step, for example.

The steps of the methods described above, taken individually, are common in the field of extractions of active ingredients from natural raw materials and a person skilled in the art is able to adjust the reaction parameters based on their general knowledge, and so as to obtain the features of the active ingredient that is the subject matter of the invention.

The active ingredient comprising at least one hydrolysate of water lily flowers can be used for cosmetic uses by topical application on the skin of healthy individuals for improving the quality of the skin, and particularly for improving complexion radiance.

The active ingredients comprising extracts, preferably aqueous extracts, obtained from water lily flowers, and particularly the active ingredients according to the invention, are preferably used in cosmetic compositions comprising a cosmetically acceptable medium. These are compositions in different galenic forms, adapted for topical application on the skin.

These compositions particularly can be in the form of oil-in-water emulsions, water-in-oil emulsions, multiple emulsions (Water/Oil/Water or Oil/Water/Oil), which optionally can be microemulsions or nanoemulsions, or in the form of solutions, suspensions, hydrodispersions, aqueous gels or powders. They can be more or less fluid and assume the aspect of creams, emulsions or gels or any other aspects of healthy skin care cosmetics.

It can involve compositions comprising at least 0.1% of the liquid active ingredient according to the invention, preferably between 0.5 and 10%, or comprising at least 0.01% of a solid active ingredient (preferably powder) according to the invention.

These compositions comprise, besides the active ingredient, a physiologically acceptable and preferably cosmetically acceptable medium, i.e. which does not cause feelings of discomfort for the user, such as redness, tightness or tingling.

The compositions according to the invention can contain, as adjuvant, at least one compound selected from:
  oils, which can be particularly selected from silicone oils, linear or cyclic, volatile or non-volatile;
  waxes, such as ozokerite, polyethylene wax, beeswax or carnauba wax;
  silicone elastomers;
  surfactants, preferably emulsifiers, whether they are non-ionic, anionic, cationic or amphoteric;
  co-surfactants, such as linear fatty alcohols;
  thickeners and/or gelling agents;
  humectants, such as polyols such as glycerin;
  dyes, preservatives, fillers;
  tensors;
  sequestering agents;
  perfumes;
  and the mixtures thereof, without this list being exhaustive. Examples of such adjuvants are particularly cited in the CTFA Dictionary (International Cosmetic Ingredient Dictionary and Handbook published by the Personal Care Product Council).

Of course, a person skilled in the art will carefully select any additional compounds, active or non-active, and their amount, so that the advantageous properties of the mixture are not, or not substantially, impaired by the contemplated addition.

These compositions are particularly intended to be used on healthy skin, particularly for improving complexion radiance. The invention therefore also relates to a cosmetic method for treating the skin for a radiant complexion effect, which involves the topical application of such a composition on the skin of a healthy individual.

In order to illustrate the cosmetic effects on healthy skin of active ingredients comprising extracts, preferably aqueous extracts, obtained from water lily flowers, in particular of active ingredients comprising at least one water lily flower hydrolysate, examples and test results are provided hereafter.

EXAMPLES

Example 1: Example of an Active Ingredient According to the Invention in Liquid Form The active ingredient is obtained by implementing the following steps:
  solubilizing powder of *Nymphaea alba* flowers to 100 g/L in water;
  enzymatic hydrolysis using a carbohydrate and a protease;
  separation of the soluble and insoluble phases;
  enzymatic inactivation of the soluble phase by heat treatment;
  filtrations;
  sterilizing filtration.

The active ingredient that is obtained has the following analytical features:
  a dry matter content of 29 g/L;
  it does not contain polyphenol or it presents a total polyphenol content of less than 0.2% (detection threshold);
  a carbohydrate fraction representing 51% by total weight of dry matter;
  a protein fraction of 10% by total weight of dry matter; and
  39% of minerals by total weight of dry matter.

Example 2: Example of an Active Ingredient According to the Invention in Liquid Form The active ingredient is obtained by implementing the following steps:
  solubilizing powder of *Nymphaea alba* flowers in water;
  enzymatic hydrolysis using a single carbohydrase;
  separation of the soluble and insoluble phases;
  enzymatic inactivation of the soluble phase by heat treatment;
  filtrations;
  sterilizing filtration.

Example 3: Example of a Composition According to the Invention

An example of a formulation containing an active ingredient according to the invention is presented in the following table:

TABLE 1

| | |
|---|---|
| Isononyl isononanoate (Lanol 99, Seppic) | 5.0% |
| Hydrolysate according to example 1 | 3.0% |
| Arachidyl alcohol/Behenyl Alcohol/Arachidyl glucoside (Montanov 202, Seppic) | 3.0% |
| Cetearyl alcohol/Cetearyl glucoside (Montanov 68, Seppic) | 2.0% |
| Preservatives | 0.7% |
| Polyacrylamide/C13-14 isoparaffin/Laureth-7 (Sepigel 305, Seppic) | 0.3% |
| Water | qsp 100% |

Effect of the Active Ingredient According to the Invention on Complexion Radiance The aim of this study was to evaluate the efficacy, in vivo, of the cosmetic composition of example 3, compared with a placebo, on complexion radiance.

The study was conducted on 19 healthy female volunteers aged from 35 to 55, with an average age of 43±6 years, selected for a dull complexion.

The complexion radiance study was performed as a double-blind test by two experts previously trained to judge different parameters representing skin radiance, before and after 28 days of treatment. This is a comparative study for which the subjects were their own reference.

The evaluation was carried out on a scale of scores between 1 and 10 and the parameters selected for this study were the following:

the skin grain: any irregularities on the surface of the skin are related to a dull complexion.

The parameter studied is the total surface area of objects detected in mm2 over a 10×10 mm area of interest. A high value for this parameter is characteristic of an irregularity of the cutaneous surface. The skin grain of the volunteers is thus assessed using the characteristic 1/S, which, if it increases, means that the skin grain is refined;

the transparency of the skin that allows veinlets to be seen through the skin. The finer the skin, the more it lets through the natural light of the skin, which provides a healthy-looking effect;

the radiance of the skin is characteristic of a radiant complexion. The higher the intensity of any light caught on the prominent areas of the face, the brighter the skin;

the light pink color is characteristic of a radiant complexion. The higher the pink intensity, the brighter the skin.

The volunteers applied twice a day (morning and evening), by lightly massaging until penetration, the cosmetic composition of example 3 on one half of the face, while the other half of the face received the placebo.

Table 2 (effect of the cosmetic composition of example 3 compared to the placebo on the characteristic parameters of the complexion after 28 days of a twice daily application) summarizes the results obtained with respect to the placebo for each characteristic parameter of the complexion with the cosmetic composition of example 3.

TABLE 2

| | Variation/Placebo (%) |
|---|---|
| Skin grain | +5.5% |
| | (p = 0.0388) |
| Transparency | +4.2% |
| | (p = 0.0125) |
| Radiance | +7.5% |
| | (p = 0.0025) |
| Light pink color | +10.2% |
| | (p = 0.0343) |

These results show that under the test conditions, compared with the placebo, after 28 days of twice-daily application, the formula according to example 3 improved complexion radiance:

significant increase in skin grain by 5.5% (p=0.0388). This effect was observed in 74% of the volunteers;

significant increase in skin transparency by 4.2% (p=0.0125). This effect was observed in 58% of the volunteers;

significant increase in skin radiation by 7.5% (p=0.0025). This effect was observed in 84% of the volunteers;

significant increase in the light pink color by 10.2% (p=0.0343). This effect was observed in 68% of the volunteers.

Thus, the cosmetic composition containing the active ingredient according to the invention promotes the improvement of all the characteristic parameters of the complexion.

Subjective Evaluation of the Effectiveness on the Complexion

The purpose of this study was to evaluate, in vivo, the efficacy of the active ingredient according to the invention, formulated according to example 3, by using subjective evaluation questionnaires.

The study was conducted on 19 healthy female volunteers between 35 and 55, with an average age of 43±6 years, selected for their dull complexion.

This was a double-blind test, comparative study, in which the subjects were their own reference.

The sensations felt during the twice-daily use of the cosmetic composition of example 3, compared with the placebo, for 28 days were determined using a subjective evaluation questionnaire.

The volunteers had to select one possible response from between "strongly disagree", "disagree", "agree" and "totally agree" for a set of statements:

with the emulsion my skin is brighter;
with the emulsion my complexion is more radiant;
with the emulsion my skin grain is finer;
with the emulsion my skin is revitalized;
with the emulsion my wrinkles are lessened;
with the emulsion my skin is softer;
the emulsion reduces signs of fatigue;
with the emulsion my complexion is even;
with the emulsion my complexion is more transparent;
with the emulsion my complexion is bright;
with the emulsion my complexion is clearer.

The results were analyzed by combining the "agree" and "totally agree" responses.

The results of the subjective evaluation on the effectiveness of the cosmetic composition of example 3, are summarized in Table 3 (subjective evaluation of the cosmetic composition of example 3 after twice-daily application over 28 days).

TABLE 3

| | Cosmetic composition of Example 3 |
|---|---|
| With the emulsion my skin is brighter | 83% |
| With the emulsion my complexion is more radiant | 78% |
| With the emulsion my skin grain is finer | 72% |
| With the emulsion my skin is revitalized | 89% |
| With the emulsion my wrinkles are lessened | 72% |
| With the emulsion my skin is softer | 83% |
| The emulsion reduces signs of fatigue | 78% |
| With the emulsion my complexion is even | 94% |
| With the emulsion my complexion is more transparent | 47% |
| With the emulsion my complexion is bright | 44% |
| With the emulsion my complexion is clearer | 50% |

It has been observed that under the conditions of the study, after 28 days of twice-daily application:

83% of the volunteers stated that their skin was brighter on the side treated with the active ingredient according to the invention;

78% of volunteers stated that their skin was more radiant on the side treated with the active ingredient according to the invention;

a significant majority (more than 70%) noticed a general improvement of the skin, particularly experiencing a finer grain, revitalized skin, a lessening of wrinkles, softer skin and reduced signs of fatigue;

furthermore, 94% of the volunteers found that their complexion was even after using the formula containing the active ingredient according to the invention;

finally, for almost half of the volunteers the use of the formula containing the active ingredient according to the invention has made their complexion more transparent, bright and clear.

Evaluation of the Effectiveness on Microrelief

The aim of the study was to evaluate, in vivo, the effect of the active ingredient according to the invention on microrelief. The study was carried out on volunteers who apply the cosmetic composition of example 3 and its placebo as a half-face application for 28 days. The evaluation was carried out using the fringe projection technique that uses the principle of interferometry.

The method involved projecting an array of fringes on a reference plane and on the skin to be analyzed. The fringes were deformed proportionally to the relief of the skin and the light reflected by the skin was compared to the reference surface.

The parameters studied were:
Sa: the arithmetic mean of roughness;
Sq: the root mean square of roughness.

The reduction of these parameters is characteristic of the improvement of the microrelief of the examined surface.

The operating protocol is described hereafter.

Between D-14 and D0, the volunteers applied the placebo to the entire face. On D0, the volunteers did not apply the product. The parameters were measured in the vicinity of the 'crow's feet'.

Between D1 and D27, the 19 volunteers applied the cosmetic composition of example 3 twice a day (morning and evening) on half of the face, while the other half of the face received the placebo, for 28 days by lightly massaging until penetration.

On D28, the parameters are measured in the vicinity of the 'crow's feet'.

Table 4 (Effect of the active ingredient according to the invention on microrelief of the skin on 'crow's feet' compared to the placebo after 28 days of twice-daily application) summarizes the results of the parameters characteristic of the effect of the active ingredient according to the invention on the microrelief of the skin in the vicinity of the 'crow's feet' compared to the placebo.

TABLE 4

| | Variation/Placebo (%) |
|---|---|
| Sa | −3.8% |
| | (p = 0.0501) |
| Sq | −3.5% |
| | (p = 0.0655) |

These results show that, compared with the placebo, after 28 days of twice-daily application, the cosmetic composition of example 3 lessens the microrelief of the 'crow's feet'.

Thus, the active ingredient according to the invention at 3% smooths cutaneous microrelief.

Effect of the Active Ingredient According to the Invention on the Formation of Ex Vivo Oxidized Proteins The aim of this study was to evaluate, ex vivo, the effect of the active ingredient, according to the invention, of example 1 for preserving the skin against an attack of the environmental stresses type, such as UVs. To this end, an assay of oxidized proteins following the attack was produced.

This effect was also evaluated for the extract according to example 2.

The labeling of the oxidized proteins was performed on *stratum corneum* samples, produced using an adhesive, on healthy female volunteers with normal skin on the forearms.

The samples were brought into contact, for 24 hours, with one of the extracts in an aqueous solution at 3% or in distilled water.

The following tests were studied (each result includes an average of 6 samples):

6 samples treated with the active ingredient according to the invention of example 1 at 3% in an aqueous solution, subjected to irradiation for 24 hours;

6 samples treated with the extract of example 2 at 3% in an aqueous solution, subjected to irradiation for 24 hours;

6 samples placed in distilled water subjected to irradiation for 24 hours (irradiated reference).

The samples thus prepared were subjected to artificial irradiation using a solar simulator.

6 samples treated with the active ingredient according to the invention of example 1 at 3% in an aqueous solution, and kept away from light for 24 hours;

6 samples treated with the extract of example 2 at 3% in an aqueous solution, and kept away from light for 24 hours;

6 samples placed in distilled water and kept away from light for 24 hours (non-irradiated reference).

The oxidized proteins are directly labeled on the previously dried adhesive, using a solution of fluorescein-5-thiosemicarbazide (FTZ), a specific label for carbonyl groups.

FTZ labeling allows evaluation of the amount of oxidized proteins present in the sample. The higher the level of oxidized proteins in the *Stratum corneum* sample, the greater the fluorescence in the green wavelength.

The fluorescence of each sample was observed by means of a fluorescence microscope equipped with a CCD camera linked to image analysis software. Four representative acquisitions of each sample were completed.

The effect of the irradiation on the samples placed in distilled water or treated with the active ingredient according to the invention of example 1 or the extract of example 2 was evaluated by studying the rate of change between the irradiated samples and those that were not irradiated, expressing the effect of artificial UVs on the rate of oxidized proteins.

$$\Delta \text{Irradié/Non irradié } (\%) = \frac{(VM_{irradié} - VM_{non\ irradié})}{VM_{non\ irradié}} \quad [\text{Math. 1}]$$

With:

$VM_{non\text{-}irradiated}$: being an average value on samples not subject to artificial UVs radiation;

$VM_{irradiated}$: being an average value on samples subject to artificial UVs.

The effect of each extract relative to the reference was evaluated by differentiating between the rate of change of the extract and that of the reference:

$$\Delta/\text{Témoin } (\%) = (\Delta\text{Irradié/Non irradié})_{Produit} - (\Delta\text{Irradié/Non irradié})_{Témoin} \quad [\text{Math. 2}]$$

With:

(Δ Irradiated/Non-irradiated)$_{Product}$: being the rate of change compared to non-irradiated samples treated with one of the products;

(Δ Irradiated/Non-irradiated)$_{Reference}$: being the rate of change compared to non-irradiated samples placed in distilled water.

A summary of the results corresponding to the effect of the active ingredient, according to the invention, of example 1 and of the extract of example 2, compared with the reference, on the formation of oxidized proteins under the action of artificial UVs, is shown in Table 5 (Effect of various extracts at 3% on the formation of oxidized proteins under the action of artificial UVs, compared with distilled water).

TABLE 5

|  | Variation/Reference (%) |
| --- | --- |
| Excerpt from example 1 at 3% | −52.5 |
| Excerpt from example 2 at 3% | −15.8 |

Under the conditions of this study, it has been observed that the two active ingredients according to the invention limit the formation of oxidized proteins generated by artificial irradiation compared to the reference, but it has been observed that this effect is much greater with the hydrolysate of example 1.

What is claimed is:

1. A cosmetic active ingredient comprising at least one hydrolysate from an aqueous extract of *Nymphaea alba* flowers, wherein the hydrolysate comprises at least 23% of carbohydrates by weight of dry matter of the hydrolysate.

2. The cosmetic active ingredient according to claim 1, characterized in that the hydrolysate comprises carbohydrates, minerals and peptides.

3. The cosmetic active ingredient according to claim 1, characterized in that the hydrolysate comprises at least 30% of minerals by weight of dry matter of the hydrolysate.

4. The cosmetic active ingredient according to claim 1, characterized in that the hydrolysate comprises at least 8% of peptides by weight of dry matter of the hydrolysate.

5. The cosmetic active ingredient according to claim 1, characterized in that the peptides present in the hydrolysate have molar masses of less than 2000 Da.

6. The cosmetic active ingredient according to claim 1, characterized in that it is in liquid form.

7. The cosmetic active ingredient according to claim 1, characterized in that it is exclusively formed by the hydrolysate.

8. The cosmetic active ingredient according to claim 6, characterized in that the dry matter content of the hydrolysate is between 22 and 55 g/l.

9. The cosmetic active ingredient according to claim 1, characterized in that it is in solid form.

10. The cosmetic active ingredient according to claim 9, characterized in that it is formed at least by the hydrolysate in solid form and by a carrier.

11. The cosmetic active ingredient according to claim 1, characterized in that the hydrolysate comprises less than 0.2% of polyphenols by weight of dry matter of the hydrolysate.

12. The cosmetic active ingredient according to claim 1, characterized in that it is an enzymatic hydrolysate.

13. A method for obtaining an active ingredient according to claim 1, characterized in that it comprises at least one step of hydrolysis of *Nymphaea alba* flowers.

14. The method according to claim 13, characterized in that the hydrolysis step comprises at least two enzymatic hydrolyses each carried out with at least one enzyme, said enzymes being of different types.

15. The method according to claim 13, characterized in that it comprises implementing the following steps:

solubilization of powder of *Nymphaea alba* flowers in water;

enzymatic hydrolyses using at least two different types of enzymes;

separation of the soluble and insoluble phases;

enzymatic inactivation by heat treatment;

filtrations;

sterilizing filtration.

\* \* \* \* \*